(12) United States Patent
Hilscher et al.

(10) Patent No.: US 9,983,153 B2
(45) Date of Patent: May 29, 2018

(54) SYSTEM AND METHOD FOR REAL TIME ON-STREAM ANALYSIS OF OIL SANDS COMPOSITION

(71) Applicant: Sacré-Davey Innovations Inc., North Vancouver (CA)

(72) Inventors: Brent Max Hilscher, Surrey (CA); Na Woong Yoon, Vancouver (CA)

(73) Assignee: Sacré-Davey Innovations Inc., North Vancouver (CA)

( * ) Notice: Subject to any disclaimer, the term of this patent is extended or adjusted under 35 U.S.C. 154(b) by 0 days. days.

(21) Appl. No.: 15/643,772

(22) Filed: Jul. 7, 2017

(65) Prior Publication Data

US 2018/0011036 A1    Jan. 11, 2018

(30) Foreign Application Priority Data

Jul. 7, 2016  (CA) .................................... 2935712

(51) Int. Cl.
*G01N 23/222* (2006.01)
*G01N 22/04* (2006.01)

(52) U.S. Cl.
CPC .......... *G01N 23/222* (2013.01); *G01N 22/04* (2013.01); *G01N 2223/0745* (2013.01); *G01N 2223/616* (2013.01); *G01N 2223/643* (2013.01)

(58) Field of Classification Search
CPC .......... G01N 22/04; G01N 2223/0745; G01N 2223/616; G01N 2223/643; G01N 23/222
See application file for complete search history.

(56) References Cited

U.S. PATENT DOCUMENTS

| 8,547,096 B2 * | 10/2013 | Kamar | ................ G01N 24/081 324/307 |
| 2014/0110590 A1 * | 4/2014 | Dep | ...................... G01N 23/09 250/363.01 |
| 2014/0347472 A1 * | 11/2014 | Davis | ................ G01N 21/3563 348/135 |

FOREIGN PATENT DOCUMENTS

| CA | 2672018 A1 | 3/2010 |
| CA | 2834980 A1 | 5/2014 |
| CA | 2909029 A1 | 12/2015 |
| CN | 101334380 A | 12/2008 |

* cited by examiner

*Primary Examiner* — Mark R Gaworecki
(74) *Attorney, Agent, or Firm* — Seed IP Law Group LLP

(57) ABSTRACT

A method for real time on-stream analysis of oil sands composition is disclosed comprising the steps of detecting a moisture content of an oil sands stream using a microwave transmission analyzer, detecting an elemental composition of the oil sands stream using a prompt gamma neutron activation analyzer and calculating a content of hydrocarbons, clays and sands in the oil sands stream. The total clay amount in the oil sands stream is based on the detected gamma spectra of several elemental components of the oil sands stream, such as sodium, magnesium, potassium, calcium and iron.

20 Claims, 1 Drawing Sheet

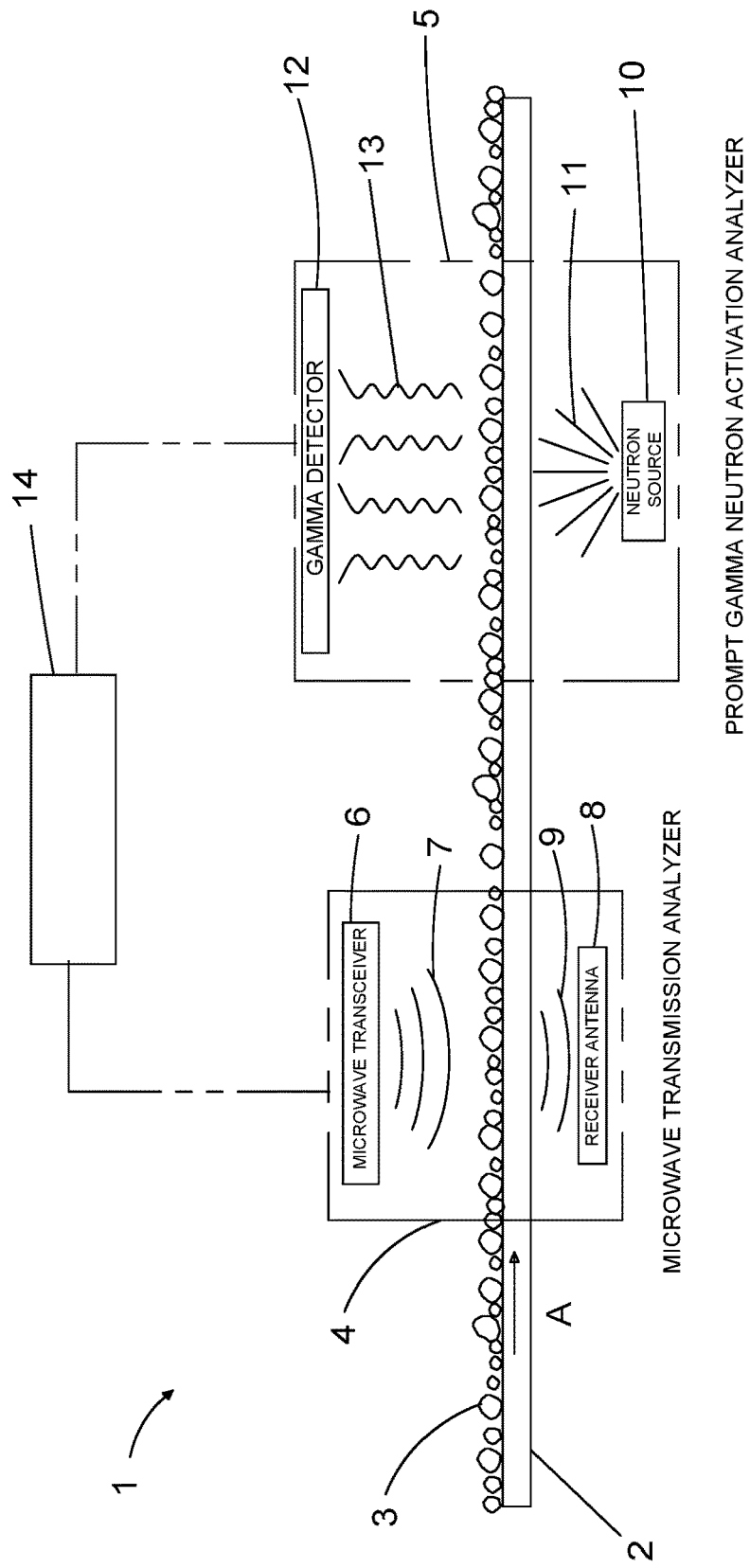

SYSTEM AND METHOD FOR REAL TIME ON-STREAM ANALYSIS OF OIL SANDS COMPOSITION

TECHNICAL FIELD

The present invention relates to a system and a method for real time on-stream analysis of oil sands composition, more specifically to a system and a method for analyzing in real-time the content of an oil sands stream in regards to its four main components (water, clays, sands and hydrocarbons).

BACKGROUND

Oil sands are mined from the ground and fed to conveyors forming a stream that is processed downstream for extracting bitumen to produce oil. The stream of oil sands is composed of four main components: sands (e.g. quartz sand), water, clay and heavy oil or hydrocarbons (called bitumen). Calculating accurately the amounts of each of these components present in the oil sands stream is important because it can help predict and improve the extraction recovery of oil sands and control the oil production process. For example, clay seams are common and interfere with the conventional extraction methods and it would useful to measure more accurately the amount of clays in the oil sands stream extracted from the ground.

Among the known methods used for analyzing the composition of the extracted oil sands are near infrared (NIR) and radio spectrometry. Both are used to assess the concentration of constituents in oil sands where the reflectance spectra range from 1100 nm to 2500 nm and the specific oil sands components have specific wavelengths, for example 1400 nm for water, 1720 nm for oil, 2200 nm for kaolinite. Canadian patent application number 2834980 describes, for example, a method for analyzing a bitumen-containing process stream including directing a beam of infrared light at the stream, capturing the light corresponding to the infrared light after its interaction with the bitumen-containing process stream, and analyzing the captured light to obtain a spectrum. The composition estimate can be generated based on the obtained spectrum and a calibrated model. The disadvantage of the NIR and radio spectrometry methods is that they do not measure the actual amounts of the elements present in the oil sands, but rather estimate the amounts of some individual oil sands components such as oil, water and some clays using their associated wavelengths.

Another method used in the mining industry is the spectroscopic analysis of oil sands, which uses the signals containing information about the images of the ore sample to create a real time ore grade visualization including a composite overlay image of the ore sample, as described, for example, in United States patent application number 20140347472. This technology does not measure any oil sands components, but rather estimates the grade of the oil.

Furthermore, nuclear magnetic resonance pulse spectrometry can be used to analyze oil sands composition by initially saturating the magnetization of the oil sand sample and then subjecting the samples to a sequence of radio-frequency pulses optimized for the measurement of bitumen and water in the sample, as described in U.S. Pat. No. 8,547,096. The amount of bitumen and water is determined based on a partial least squares optimization based chemometric model. This technology can not be used to obtain information about certain components that might be present in the oil sands, for example the amounts of different clays.

The oil content in oil sands can also be measured using an acoustic technique, by observing the nonlinear dissipation phenomenon that is generated by the sound wave spreading in the oil sands. The oil saturation degree of the oil sands sample can be determined from the relative growth factor G and the nonlinear dissipation factor Alpha through a backward deduction method as described for example in the Chinese patent application number 101334380. However, this method also fails to measure the information related to certain components that might be present in the oil sands, for example information related to the amount of clay material.

There are also other methods for analyzing materials extracted from an earth formation. Prompt gamma neutron activation analysis (PGNAA) is one such method that is generally used to determine metal contents of ores. PGNAA has also been used to detect a clay parameter indicating, for example, a weight percentage of clay particles in an oil sand tailings stream, as described for example in Canadian patent application number 2909029.

In another method which involves using pulse neutron spectroscopy, the composition of the hydrocarbon material in the material extracted from an earth formation can be calculated based on the at least one gamma ray spectrum detected at the pulse neutron spectroscopy tool which emits a plurality of pulses of high-energy neutrons into the portion of the hydrocarbon material diverted and stored into a container, as described in Canadian patent application 2672018.

The known methods for analyzing the oil sands composition, described above, are only estimating certain components of oil sands or can only be used for detecting the composition of oil sand samples.

Therefore, there is still a need for a system and a method for real time, on-stream analysis of oil sand composition that can measure all the components of an oil sand stream (water, sand, hydrocarbon and clay) more accurately and in a continuous manner.

SUMMARY OF THE INVENTION

The present invention describes a method for real time on-stream analysis of oil sands composition comprising the steps of:
a. detecting a moisture content of an oil sands stream using a microwave transmission analyzer, and
b. detecting an elemental composition of the oil sands stream using a prompt gamma neutron activation analyzer and calculating a content of hydrocarbons, clays and sands in the oil sands stream.

The step of detecting the moisture content of the oil sands stream comprises transmitting a microwave signal from a microwave transceiver through an oil sands stream to a receiver antenna and comparing the microwave signal transmitted by the microwave transceiver to a microwave signal received by the receiver antenna. In preferred embodiments, the step of detecting the moisture content of the oil sands stream can further comprise weighting the oil sands stream and factoring in a weight of the oil sands stream when comparing the received microwave signal to the transmitted microwave signal to calculate the moisture content in the oil sands stream.

The step of detecting the elemental composition of the oil sands stream comprises generating neutrons from a neutron source and detecting a series of gamma spectra by a gamma detector, each detected gamma spectrum corresponding to an element present in the oil sands stream.

For example, for obtaining the total hydrocarbon amount in the oil sands stream, the method comprises detecting a sulphur content in the oil sands stream as indicated by a sulphur gamma spectrum detected by the gamma detector and calculating a total hydrocarbon amount in the oil sands stream based on the detected sulphur content.

The present method also comprises calculating a total clay amount in the oil sands stream based on the detected gamma spectra of several elemental components of the oil sands stream.

Generally, the total clay amount in the oil sands stream is the sum of the total amount of illite, the total amount of vermiculite, the total amount of chlorite, the total amount of montmorillonite and the total amount of kaolinite.

For obtaining the total amount of illite in the oil sands stream, the method comprises detecting the potassium content in the oil sands stream as indicated by a potassium gamma spectrum detected by the gamma detector and calculating the total amount of illite in the oil sands stream based on the detected potassium content.

Furthermore, for obtaining the total amount of vermiculite in the oil sands stream, the method comprises detecting the total iron content in the oil sands stream as indicated by an iron gamma spectrum detected by the gamma detector and calculating the total amount of vermiculite in the oil sands stream by subtracting the amount of iron found in the total amount of illite from the total iron content in the oil sands stream.

For obtaining the total amount of chlorite in the oil sands stream, the method comprises detecting the total magnesium content in the oil sands stream as indicated by a magnesium gamma spectrum detected by the gamma detector and calculating the total amount of chlorite in the oil sands stream by subtracting the amount of magnesium found in the total amount of illite and in the total amount of vermiculite from the total magnesium content in the oil sands stream.

For obtaining the total amount of montmorillonite in the oil sands stream, the method further comprises detecting the total sodium content in the oil sands stream as indicated by a sodium gamma spectrum detected by the gamma detector and calculating the total amount of montmorillonite in the oil sands stream by subtracting the amount of sodium found in the total amount of chlorite from the total sodium content in the oil sands stream.

In other embodiments, the total amount of montmorillonite is obtained by detecting the calcium content in the oil sands stream as indicated by a calcium gamma spectrum detected by the gamma detector and calculating the total amount of montmorillonite in the oil sands stream based on the detected calcium content.

For obtaining the total amount of kaolinite in the oil sands stream, the method further comprises detecting the total aluminum content in the oil sands stream as indicated by an aluminum gamma spectrum detected by the gamma detector and calculating the total amount of kaolinite in the oil sands stream by subtracting the amount of aluminum found in the total amounts of illite, montmorillonite, chlorite and vermiculite from the total aluminum content in the oil sands stream.

In some embodiments, the total amount of hydrocarbon is obtained by detecting the total hydrogen content in the oil sands stream as indicated by a hydrogen gamma spectrum detected by the gamma detector and calculating the total hydrocarbon amount in the oil sands stream by subtracting the amount of hydrogen found in water and the amount of hydrogen found in the total clay amount from the total hydrogen content in the oil sands stream.

For obtaining the total amount of sand in the oil sands stream the method comprises detecting the total silicon content in the oil sands stream as indicated by the silicon gamma spectrum detected by the gamma detector and calculating the total amount of sand by subtracting the amount of silicon found in the total clay amount from the total silicon content in the oil sands stream.

A system for real time on-stream analysis of oil sands composition is also disclosed, the system comprising a conveyor belt on which an oil sands stream is fed, a microwave transmission analyzer for detecting the moisture content in the oil sands stream, a prompt gamma neutron activation analyzer for detecting an elemental composition of the oil sands stream and a computation unit for calculating the oil sands composition based on the detected elemental composition of the oil sands stream, wherein the microwave transmission analyzer and the prompt gamma neutron activation analyzer are connected in series.

In some embodiments, the microwave transmission analyzer is located downstream of the prompt gamma neutron activation analyzer relative to the oil sands stream flow.

In other embodiments, the microwave transmission analyzer is located upstream of the prompt gamma neutron activation analyzer relative to the oil sands stream flow.

The microwave transmission analyzer comprises a microwave transceiver and a receiver antenna.

The prompt gamma neutron activation analyzer comprises a neutron source and a gamma detector.

The present method is also useful for controlling the oil sands extraction process wherein the moisture content and the elemental composition of the oil sands stream detected according to the method described here is used for tonnage, water and middlings flowrate optimization and for controlling slurry temperature.

BRIEF DESCRIPTION OF THE DRAWINGS

The drawing illustrates a specific preferred embodiment of the invention, but should not be considered as restricting the spirit or scope of the invention in any way.

FIG. 1 shows a schematic view of a system for real time on-stream analysis of oil sands composition according to a preferred embodiment of the invention.

DETAILED DESCRIPTION

Certain terminology is used in the present description and is intended to be interpreted according to the definitions provided below. In addition, terms such as "a" and "comprises" are to be taken as open-ended.

FIG. 1 shows a schematic view of a system 1 for real time on-stream analysis of oil sands composition according to a preferred embodiment of the present invention. System 1 comprises a conveyor belt 2 which carries a stream of oil sands 3 mined from the ground, in a direction A, from the extraction site to a processing site (not illustrated).

The oil sands are composed of four main components: sand, water, clay and hydrocarbons. The sand can be quartz sand and the hydrocarbons are generally composed of heavy oil called bitumen.

As further illustrated in FIG. 1, the present system comprises a microwave transmission analyzer 4 and a prompt gamma neutron activation (PGNA) analyzer 5, which are connected in series along the conveyor belt, the microwave transmission analyzer 4 followed by the PGNA analyzer 5.

In other embodiments, the microwave transmission analyzer 4 can be placed on the other side of the PGNA analyzer 5, more specifically downstream of the PGNA analyzer with respect to the moving direction A of the conveyor belt 2.

The microwave transmission analyzer 4 comprises a microwave transceiver 6 which emits a signal, a low frequency beam 7 which is transmitted through the oil sands stream carried on the conveyor belt to a receiver antenna 8 which receives a signal 9 and compares it to the transmitted signal 7 to detect the change in phase and amplitude. The digital measurements of the microwave transmission analyzer 4 in regards to the change in phase and amplitude of the transmitted signal 7 as it passes through the oil sands stream allow a real-time, accurate measurement of the moisture in the oil sands stream passing through the microwave transmission analyzer.

The PGNA analyzer 5 comprises a neutron source 10 which generates neutrons 11 which are absorbed by the elemental nuclei in the oil sand stream carried on the conveyor belt and each of the excited elemental nuclei releases a gamma ray having an energy level related to the respective element. The PGNA analyzer further comprises a gamma detector 12 positioned above the conveyor belt 2 which records the received gamma rays 13 and displays the measurements over time as a series of spectra where the different peaks represent the different elements present in the oil sands stream carried on the conveyor belt and passing through the PGNA analyzer. In this process, the PGNA analyzer utilizes an appropriate radioisotope (e.g. Californium-252) to conduct the thermal neutron capture and gamma ray production.

The system further comprises a computation unit 14 which communicates with the microwave transmission analyzer 4 and the PGNA analyzer 5 for analyzing and calculating the oil sands composition of the oil sand stream 3 according to the method of the present invention.

The method for real time, analysis of oil sands composition comprises calculating the amounts of the main components (water, clays, hydrocarbons, and sands) in the oil sand stream carried by the conveyor belt 2, using the readings from the microwave transmission analyzer 4 and the PGNA analyzer 5.

The method comprises the steps of detecting the moisture content of the oil sands stream using the microwave transmission analyzer, detecting the elemental composition of the oil sands stream using the PGNA analyzer and further calculating in the computation unit the content of hydrocarbons, clays and sands in the oil sand stream.

The step of detecting the amount of water in the oil sands stream is determined using the microwave transmission analyzer 4. The digital measurements of the microwave transmission analyzer 4 in regards to the change in phase and amplitude of the transmitted signal 7, as it passes through the oil sands stream, allow a real-time, accurate measurement of the moisture in the oil sands stream by the computation unit 14. The change in phase and amplitude of the transmitted signal 7 is influenced by the amount of material measured and therefore the weight of the material on the conveyor belt, passing through the microwave transmission analyzer, is also measured and factored in the measurement of the moisture in the oil sands stream.

The step of detecting the elemental composition of the oil sands stream using the PGNA analyzer comprises generating neutrons from a neutron source and detecting a series of gamma spectra by the PGNA analyzer, each gamma spectrum corresponding to an element present in the oil sands stream. The amount of clays in the oil sands stream is then calculated by the computation unit based on the elemental composition indicated by the series of spectra displayed by the PGNA analyzer which represent the different elements in the material on the conveyor passing through the analyzer. A variety of clays are present in the oil sands and each type of clay is determined by the method described here. Some common clays found in oil sands include illite $(K,H_3O)(Al,Mg,Fe)_2(Si,Al)_4O_{10}[(OH)_2,(H_2O)]$, kaolinite $Al_2Si_2O_5(OH)_4$, and montmorillonite $Na_{0.2}Ca_{0.1}Al_2Si_4O_{10}(OH)_2(H_2O)_{10}$. Some less common clays include chlorite $Na_{0.5}Al_4Mg_2Si_7AlO_{18}(OH)_{12}.5(H_2O)$ and vermiculite $Mg_{1.8}Fe^{2+}_{0.9}Al_{4.3}SiO_{10}(OH)_2.4(H_2O)$.

The amount of illite in the oil sands is calculated based on the potassium content indicated by the potassium gamma spectrum detected by the PGNA analyzer.

The amount of vermiculite in the oil sands stream is based on the total iron content in the oil sands stream indicated by the iron gamma spectrum detected by the PGNA analyzer and is calculated by subtracting the amount of iron found in the calculated amount of illite from the total iron content in the oil sands stream, since illite and vermiculite are the only clay minerals that contain iron.

The amount of chlorite in the oil sands stream is based on the total magnesium content in the oil sands stream indicated by the magnesium gamma spectrum detected by the PGNA analyzer and is calculated by subtracting the sum of the amounts of magnesium found in the calculated amounts of illite and vermiculite from the total magnesium content in the oil sands stream detected by the PGNA analyzer, since illite, vermiculite and chlorite are the only clay minerals that contain magnesium.

The amount of montmorillonite in the oil sands stream is based on the total sodium content in the oil sand stream indicated by the sodium gamma spectrum detected by the PGNA analyzer and is calculated by subtracting the amount of sodium found in the calculated amount of chlorite from the total sodium content in the oil sands stream detected by the PGNA analyzer, since montmorillonite and chlorite are the only clay minerals that contain sodium.

Alternatively, in other embodiments, the amount of montmorillonite in the oil sands stream can be calculated based on the total calcium content in the oil sand stream indicated by the calcium gamma spectrum detected by the PGNA analyzer, since montmorillonite is the only oil sands clay with calcium in its mineral composition.

The amount of kaolinite in the oil sands stream is based on the total aluminum content in the oil sand stream indicated by the aluminum gamma spectrum detected by the PGNA analyzer and is calculated by subtracting the amount of aluminum found in the calculated amounts of illite, montmorillonite, chlorite and vermiculite from the total aluminum content in the oil sands stream detected by the PGNA analyzer.

The total amount of clays in the oil sands stream is then determined by adding the amounts of illite, vermiculite, chlorite, montmorillonite and kaolinite, calculated in the previous steps.

Table 1 below shows the breakdown of the composition of common clays found in oil sands.

TABLE 1

|  | Molecular Weight [g/mol] | Al % | Si % | H % | Mg % | Fe % | K % | Ca % | Na % |
| --- | --- | --- | --- | --- | --- | --- | --- | --- | --- |
| Illite | 389.34 | 9.01 | 25.25 | 1.35 | 1.87 | 1.43 | 6.03 | — | — |
| Kaolinite | 258.16 | 20.90 | 21.76 | 1.56 | — | — | — | — | — |
| Montmorillonite (Smectite) | 549.07 | 9.83 | 20.46 | 4.04 | — | — | — | 0.73 | 0.84 |
| Chlorite | 973.76 | 13.85 | 20.19 | 2.28 | 4.99 | — | — | — | 1.18 |
| Vermiculite | 504.19 | 23.01 | 5.51 | 2.00 | 8.86 | 9.97 | — | — | — |

The amount of hydrocarbons in the oil sand stream is calculated based on the sulphur content indicated by the sulphur gamma spectrum detected in the oil sands stream by the PGNA analyzer.

Alternatively, in other embodiments, the amount of hydrocarbons in the oil sand stream can be calculated based on the total hydrogen content indicated by the hydrogen gamma spectrum detected by the PGNA analyzer and is calculated by subtracting the amount of hydrogen found in water, and in the clays from the total hydrogen content in the oil sands stream detected by the PGNA analyzer.

Further, the amount of sand in the oil sands stream is calculated based on the silicon content indicated by the silicon gamma spectrum detected in the oil sands stream by the PGNA analyzer and is calculated by subtracting the amount of silicon found in the total clay amount from the total silicon content detected in the oil sands stream by the PGNA analyzer.

A person skilled in the art would easily understand that the amounts of the different elements in the oil sands stream can be calculated differently depending on the presence of different clay minerals in the oil sands stream and that the steps of the method described above vary depending on the oil sands stream composition. For example, if it is known that the oil sand stream does not contain chlorite, the step of determining the amount of chlorite from the present method will be skipped.

A person skilled in the art would easily understand that in the present disclosure and in the claims the term "found", as for example in the sentence "the amount of iron found in the total amount of illite" should be interpreted to mean the amount of iron in the total amount of illite, which is calculated based on correspondence tables, known in the art, such as Table 1 presented in this disclosure.

The present method is useful for controlling the oil sands extraction process wherein the moisture content and the elemental composition of the oil sands stream obtained according to the present method is used for tonnage, water and middlings flowrate optimization and for controlling slurry temperature.

The advantages of the present invention are that the method of the present invention comprising the PGNA and microwave transmission technology can accurately measure the main components of an oil sand stream, in a continuous manner where the oil sand stream is carried by a moving conveyor belt. The PGNA analyzer measures all the atomic elements present in the oil sands and the computation unit calculates the total amount of each component of the oil sands stream.

While particular elements, embodiments and applications of the present invention have been shown and described, it will be understood, of course, that the invention is not limited thereto since modifications may be made by those skilled in the art without departing from the spirit and scope of the present disclosure, particularly in light of the foregoing teachings. Such modifications are to be considered within the purview and scope of the claims appended hereto.

What is claimed is:

1. A method for real time on-stream analysis of oil sands composition comprising the steps of:
    a) detecting a moisture content of an oil sands stream using a microwave transmission analyzer, and
    b) detecting an elemental composition of the oil sands stream using a prompt gamma neutron activation analyzer and calculating a content of hydrocarbons, clays and sands in the oil sands stream.

2. The method of claim 1, wherein the step of detecting the moisture content of the oil sands stream comprises transmitting a microwave signal from a microwave transceiver through an oil sands stream to a receiver antenna and comparing the microwave signal transmitted by the microwave transceiver to a microwave signal received by the receiver antenna.

3. The method of claim 2, wherein the step of detecting the moisture content of the oil sands stream further comprises weighting the oil sands stream and factoring in a weight of the oil sands stream when comparing the received microwave signal to the transmitted microwave signal.

4. The method of claim 1, wherein the step of detecting the elemental composition of the oil sands stream comprises generating neutrons from a neutron source and detecting a series of gamma spectra by a gamma detector, each detected gamma spectrum corresponding to an element present in the oil sands stream.

5. The method of claim 1, comprising detecting a sulphur content in the oil sands stream as indicated by a sulphur gamma spectrum detected by the gamma detector and calculating a total hydrocarbon amount in the oil sands stream based on the detected sulphur content.

6. The method of claim 1, comprising calculating a total clay amount in the oil sands stream based on the detected gamma spectra of several elemental components of the oil sands stream.

7. The method of claim 6, wherein the total clay amount in the oil sands stream is the sum of a total amount of illite, a total amount of vermiculite, a total amount of chlorite, a total amount of montmorillonite and a total amount of kaolinite.

8. The method of claim 7, further comprising detecting a potassium content in the oil sands stream as indicated by a potassium gamma spectrum detected by the gamma detector and calculating the total amount of illite in the oil sands stream based on the detected potassium content.

9. The method of claim 8, further comprising detecting a total iron content in the oil sands stream as indicated by an iron gamma spectrum detected by the gamma detector and calculating the total amount of vermiculite in the oil sands stream by subtracting an amount of iron found in the total amount of illite from the total iron content in the oil sands stream.

10. The method of claim 9, further comprising detecting a total magnesium content in the oil sands stream as indicated by a magnesium gamma spectrum detected by the gamma detector and calculating the total amount of chlorite in the oil sands stream by subtracting an amount of magnesium found in the total amount of illite and in the total amount of vermiculite from the total magnesium content in the oil sands stream.

11. The method of claim 10, further comprising detecting a total sodium content in the oil sands stream as indicated by a sodium gamma spectrum detected by the gamma detector and calculating the total amount of montmorillonite in the oil sands stream by subtracting an amount of sodium found in the total amount of chlorite from the total sodium content in the oil sands stream.

12. The method of claim 11, further comprising detecting a total aluminum content in the oil sands stream as indicated by an aluminum gamma spectrum detected by the gamma detector and calculating the total amount of kaolinite in the oil sands stream by subtracting an amount of aluminum found in the total amounts of illite, montmorillonite, chlorite and vermiculite from the total aluminum content in the oil sands stream.

13. The method of claim 7, further comprising detecting a calcium content in the oil sands stream as indicated by a calcium gamma spectrum detected by the gamma detector and calculating the total amount of montmorillonite in the oil sands stream based on the detected calcium content.

14. The method of claim 6, further comprising detecting a total hydrogen content in the oil sands stream as indicated by a hydrogen gamma spectrum detected by the gamma detector and calculating a total hydrocarbon amount in the oil sands stream by subtracting an amount of hydrogen found in water and an amount of hydrogen found in the total clay amount from the total hydrogen content in the oil sands stream.

15. The method of claim 6, further comprising detecting a total silicon content in the oil sands stream as indicated by a silicon gamma spectrum detected by the gamma detector and calculating a total amount of sand by subtracting an amount of silicon found in the total clay amount from the total silicon content in the oil sands stream.

16. The method of claim 7, further comprising the steps of:
  a) detecting a potassium content in the oil sands stream as indicated by a potassium gamma spectrum detected by the gamma detector and calculating the total amount of illite in the oil sands stream based on the detected potassium content;
  b) detecting a total iron content in the oil sands stream as indicated by an iron gamma spectrum detected by the gamma detector and calculating the total amount of vermiculite in the oil sands stream by subtracting an amount of iron found in the total amount of illite from the total iron content in the oil sands stream;
  c) detecting a total magnesium content in the oil sands stream as indicated by a magnesium gamma spectrum detected by the gamma detector and calculating the total amount of chlorite in the oil sands stream by subtracting an amount of magnesium found in the total amount of illite and in the total amount of vermiculite from the total magnesium content in the oil sands stream;
  d) detecting a total sodium content in the oil sands stream as indicated by a sodium gamma spectrum detected by the gamma detector and calculating the total amount of montmorillonite in the oil sands stream by subtracting an amount of sodium found in the total amount of chlorite from the total sodium content in the oil sands stream, or
  detecting a total calcium content in the oil sands stream as indicated by a calcium gamma spectrum detected by the gamma detector and calculating the total amount of montmorillonite in the oil sands stream based on the detected total calcium content;
  e) detecting a total aluminum content in the oil sands stream as indicated by an aluminum gamma spectrum detected by the gamma detector and calculating the total amount of kaolinite in the oil sands stream by subtracting an amount of aluminum found in the total amounts of illite, montmorillonite, chlorite and vermiculite from the total aluminum content in the oil sands stream;
  f) calculating the total amount of clays in the oil sands stream by adding the amounts of illite, vermiculite, chlorite, montmorillonite and kaolinite, calculated in the previous steps;
  g) detecting a total hydrogen content in the oil sands stream as indicated by a hydrogen gamma spectrum detected by the gamma detector and calculating a total hydrocarbon amount in the oil sands stream by subtracting an amount of hydrogen found in water and an amount of hydrogen found in the total clay amount from the total hydrogen content in the oil sands stream, or
  detecting a sulphur content in the oil sands stream as indicated by a sulphur gamma spectrum detected by the gamma detector and calculating a total hydrocarbon amount in the oil sands stream based on the detected sulphur content; and
  h) detecting a total silicon content in the oil sands stream as indicated by a silicon gamma spectrum detected by the gamma detector and calculating a total amount of sand by subtracting an amount of silicon found in the total clay amount from the total silicon content in the oil sands stream.

17. A system for real time on-stream analysis of oil sands composition comprising a conveyor belt on which an oil sands stream is fed, a microwave transmission analyzer for detecting the moisture content in the oil sands stream, a prompt gamma neutron activation analyzer for detecting an elemental composition of the oil sands stream and a computation unit for calculating the oil sands composition based on the detected elemental composition of the oil sands stream, wherein the microwave transmission analyzer and the prompt gamma neutron activation analyzer are connected in series.

18. The system of claim 17, wherein the microwave transmission analyzer is located downstream of the prompt gamma neutron activation analyzer relative to the oil sands stream flow.

19. The system of claim 17, wherein the microwave transmission analyzer is located upstream of the prompt gamma neutron activation analyzer relative to the oil sands stream flow.

20. The system of claim 17, wherein the microwave transmission analyzer comprises a microwave transceiver and a receiver antenna and the prompt gamma neutron activation analyzer comprises a neutron source and a gamma detector.

* * * * *